United States Patent [19]

Takahashi et al.

[11] Patent Number: 4,909,073
[45] Date of Patent: Mar. 20, 1990

[54] APPARATUS FOR MEASURING A RESISTANCE AGAINST SLIPPAGE ON ROAD SURFACE

[75] Inventors: Mitsuo Takahashi, Yugawara; Toshihiko Fukuhara, Hadano, both of Japan

[73] Assignee: Kabushiki Kaisha Komatsu Seisakusho, Tokyo, Japan

[21] Appl. No.: 263,948

[22] Filed: Oct. 28, 1988

[51] Int. Cl.⁴ ............................................. G01N 19/02
[52] U.S. Cl. ........................................... 73/146; 73/9; 73/8; 73/104
[58] Field of Search ...................... 73/9, 8, 146, 104

[56] References Cited

U.S. PATENT DOCUMENTS 3,538,742 11/1970 Benning ..................................... 73/9
4,662,211 5/1987 Strong ....................................... 73/9
4,723,444 2/1988 Hajek ........................................ 73/8

FOREIGN PATENT DOCUMENTS 62-265551 11/1987 Japan ......................................... 73/9
151074 3/1959 U.S.S.R. ................................. 73/146

Primary Examiner—Joseph A. Orsino
Assistant Examiner—Kinfe-Michael Negash
Attorney, Agent, or Firm—Diller, Ramik & Wight

[57] ABSTRACT

According to the present invention, an apparatus for measuring a resistance against slippage on the road surface is so constructed that two measuring wheels adapted to be rotated by imparting a tractive force to the apparatus are connected to one another via a torsion bar extending therebetween, a difference in rotation is forcibly produced by changing a rotational speed of one of the measuring wheels and a slippage resistance on the road surface is measured by detecting a torque generated on the torsion bar due to the slippage resistance on the road surface.

3 Claims, 5 Drawing Sheets

FIG.3
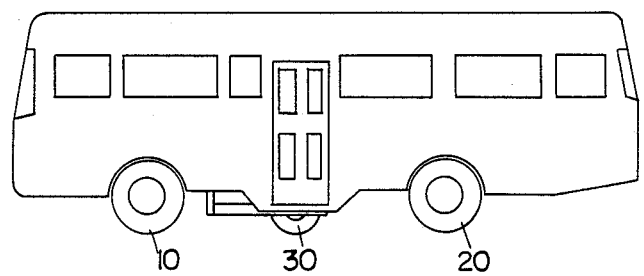
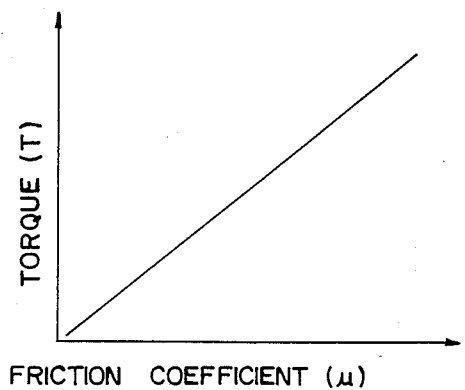
FIG.4

APPARATUS FOR MEASURING A RESISTANCE AGAINST SLIPPAGE ON ROAD SURFACE

FIELD OF THE INVENTION

The present invention relates to an apparatus for measuring a resistance against slippage on the road surface.

DESCRIPTION OF THE PRIOR ART

When slippage is liable to occur on the surface of an asphalt-paved road, tires on a motorcar are caused to slip at a time of quick stop, outrunning or running along a curve, which tends to cause a traffic accident.

In view of the foregoing traffic accident, a slippage resistance coefficient on the road surface is measured to know the current extent of tendency of causing slippage on the paved road.

Pursuant to regulations in Japan, a position where a slippage resistance coefficient on the road surface is measured is normally located at the center of a right-hand wheel track on the running road. On the contrary, pursuant to regulations in U.S.A., the measuring position is located at the center on a left-hand wheel track on the running road. To meet the regulations, various kinds of apparatuses have been developed.

As a method of measuring a slippage resistance coefficient on the road surface, the following methods have been proposed.

(i) A portable tester method in which a slippage resistance on the road surface is measured by allowing a pendulum having a rubber piece attached to the lowermost end thereof to fall down from a certain height and then measuring a height by which the pendulum bounces up above the road surface after the rubber piece rubs against it.

(ii) A trailer method in which wheels on the trailer are braked, a force required for tracting the braked wheel at a constant speed is measured and a resistance coefficient is then obtained on the basis of a friction coefficient appearing at a time of measuring the tractive force.

(iii) A deceleration method in which a simple acceleration meter is installed on a test vehicle running at a constant speed and a deceleration appearing at a time when all the wheels are locked by quick braking is measured.

(iv) A method of measuring a distance till stoppage of a test vehicle after the latter is braked wherein the test vehicle running at a constant speed is quickly braked and a distance from a position where quick braking is applied to the test vehicle to a position where the latter is completely stopped is then measured.

Among the above-described methods, each of three methods exclusive the trailer method has drawbacks that it should be practiced in such a state that a road traffic is shut off and therefore measuring is unavoidably achieved on a large scale.

In addition, the trailer method has also problems that an apparatus required for practicing the method is manufactured at an expensive cost and measuring wheels in the apparatus wear within a short period of time, although measuring can be effected during running of the apparatus.

SUMMARY OF THE INVENTION

The present invention has been made with the foregoing background in mind and its object resides in providing an apparatus for measuring a resistance against slippage on the road surface wherein a long period of running life is assured.

Other object of the present invention is to provide an apparatus measuring a resistance against slippage on the road surface wherein a slippage resistance is measured simultaneously on two lines extending on the road surface.

To accomplish the above objects, the present invention provides an apparatus for measuring a resistance against slippage on the road surface wherein speed changing means is attached to one of two measuring wheels adapted to be rotated in the same direction on the road surface to be measured while they are tracted by tracting means, shafts of the two measuring wheels are jointed to one another via a torsion bar extending therebetween, a difference in number of rotations is developed between the two measuring wheels by speed changing means and a slippage resistance appearing on the road surface is then measured by detecting a torque generated due to the slippage resistance on the road surface.

Further, the present invention provides an apparatus for measuring a resistance against slippage on the road surface wherein the apparatus includes first and second slippage resistance measuring units each of which is so constructed that speed changing means is attached to one of two measuring wheels adapted to be rotated in the same direction on the road surface to be measured while they are tracted by tracting means, shafts of the two measuring wheels are jointed to one another via a torsion bar extending therebetween, a difference in number of rotations is developed between the two measuring wheels by speed changing means and torque detecting means is provided to detect a torque on the torsion bar generated by a slippage resistance on the road surface and wherein the apparatus further includes jointing means for adjustably jointing the first and second slippage resistance measuring units to one another with a predetermined distance kept therebetween and tracting means for simultaneously tracting the first and second slippage resistance measuring units via the jointing means.

BRIEF DESCRIPTION OF THE DRAWINGS

FIG. 3 is a schematic side elevational view illustrating a second embodiment of the present invention. FIG. 4 is a diagram illustrating a relationship between torque and friction coefficient.

DESCRIPTION OF THE PREFERRED EMBODIMENTS

Now, the present invention will be described in a greater detail hereunder with reference to the accompanying drawings which illustrate preferred embodiments thereof.

Figure 1:
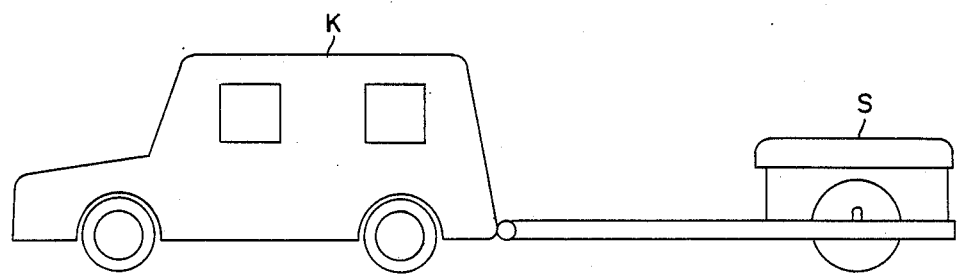
FIG. 1 is a schematic side elevational view illustrating an apparatus for measuring a resistance against slippage on the road surface in accordance with a first embodiment of the present invention.
Figure 2:
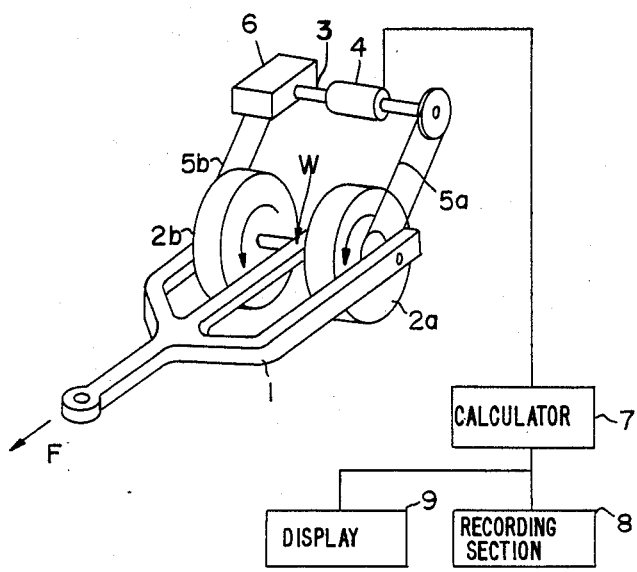
FIG. 2 is a perspective view illustrating a measuring wheel section of the apparatus.

FIG. 1 is a schematic side elevational view illustrating an apparatus for measuring a resistance against slippage on a road in accordance with an embodiment of the present invention and FIG. 2 is a perspective view illustrating a measuring wheel section of the apparatus shown in FIG. 1.

This apparatus for measuring a resistance against slippage on a road is substantially composed of a measuring wheel section S and a tractive vehicle or vehicle section K. The measuring wheel section S comprises a frame 1 operatively connected to the tractive vehicle section K, first and second measuring wheels 2a and 2b of which shaft is separately supported on the frame 1, a torsion bar 3 and a torque detector 4 for measuring a torque generated on the torsion bar 3. The first measuring wheel 2a is operatively connected to one end of the torsion bar 3 via a first chain transmission mechanism 5a, while the second measuring wheel 2b is operatively connected to the other end of the torsion bar 3 via a second chain transmission mechanism 5b and a speed change gear 6. With the above construction, the apparatus is operated such that a difference in the number of revolutions between both the measuring wheels 2a and 2b is developed by reducing the number of rotations of the second measuring wheel 2b, for instance, by 0.8 time compared with that of the first measuring wheel 2a via the speed change gear 6 and a slippage resistance appearing on the second measuring wheel 2b is then detected by the torque detector 4 in the form of a torque generated on the torsion bar 3.

An output from the torque detector 4 is transmitted to a calculator 7 adapted to calculate a slippage resistance coefficient on the basis of the detected torque. In addition, the measuring wheel section S is provided with a recording portion 8 for recording an output from the calculator 7 and a displaying portion 9 for displaying a result of measurement.

Here, reference character W designates a wheel load. The foremost end of the frame 1 is tracted by a tractive force F of the tractive vehicle K. A radius R of the first measuring wheel 2a is same to that of the second measuring wheel 2b and it is assumed that the speed change gear 6 has a gear ratio of 1:0.8.

Next, operation of the apparatus will be described below.

As the frame 1 is tracted by the tractive force F of the tractive vehicle K, the first measuring wheel 2a is rotated. A rotational force of the first measuring wheel 2a is transmitted to the torsion bar 3 via the first chain transmission mechanism 5a and it is transmitted further to the second chain mechanism 5b via the torsion bar 3 and the speed change gear 6 by which the rotational speed is reduced. Consequently, the rotational force is imparted to the second measuring wheel 2b.

And, this rotational force is transmitted to the road surface.

Due to the fact that a certain amount of difference in rotation is developed between the first measuring wheel 2a and the second measuring wheel 2b, a torque corresponding to a magnitude of friction coefficient appearing on the road surface is generated on the torsion bar 3.

This torque T is measured by the torque detector 4 so that a frictional coefficient $\mu$, that is, a slippage resistance coefficient is calculated in the calculator 7 on the basis of the measured torque T and it is then displayed on the displaying portion 9 while it is recorded in the recording portion 8.

In this manner, a slippage resistance coefficient can be measured without any hindrance given to road traffic, while the measuring wheel section S runs on the road.

This measuring principle is shown in the following. Specifically, the first and second measuring wheels run on the road surface while they are rotated under the effect of the tractive force. In a case where no speed changing means is provided, both the measuring wheels are rotated at the same speed whereby no torque is generated on the torsion bar.

However, when either of the measuring wheels is accelerated or decelerated by speed changing means, the measuring wheel having a lower rotational speed is tracted by a rotational force of the measuring wheel having a higher rotational speed, resulting in a slippage occuring on the road surface. Thus, a torque is generated in proportion to the slippage resistance at this moment on the torsion bar by way of which rotational shafts of both the measuring wheels are connected to one another. FIG. 4 is a diagram illustrating a relationship between the torque and the friction resistance.

This torque can be represented by the following formula.

$$T = A \times \mu \times W \times R$$

where $\mu$: friction coefficient on the road surface
W: wheel load
R: radius of the measuring wheel
A: coefficient relative to a power transmission loop Accordingly, the road friction coefficient $\mu$ can be calculated by measuring the torque T.

In this manner, the present invention assures that a slippage resistance can be measured without any necessity for quick braking as seen in the conventional measuring method, while the measuring wheels run on the road surface. By virtue of no quick braking being required, the measuring wheels wear few and thereby the apparatus enjoys a very long period of running life.

Additionally, since it suffices that only a torque is detected, the apparatus becomes simple in structure and it can be designed in smaller dimensions.

Further, since the tracting section is equipped with no measuring means, any influence does not appear due to a difference in kind or type among tracting sections. Thus, a measured value having a high reliability can be obtained.

Incidentally, due to the fact that a slippage resistance should be measured at a position located by about one meter outwardly of a lane mark or a center line on the road and it is necessary that a friction coefficient on the road surface with which both the measuring wheels come in contact has no difference therebetween, it is preferable that a distance between both the measuring wheels is narrow.

In the first embodiment, description has been made as to an apparatus of the type including a measuring wheel section to be tracted by a tractive vehicle. However, the present invention should not be limited only to this.

Alternatively, as a second embodiment of the present invention, an apparatus of the bus type as shown in FIG. 3 is advantageously employable which includes a measuring wheel section 30 between fore wheels 10 and rear wheels 20 of the bus.

Figure 5:
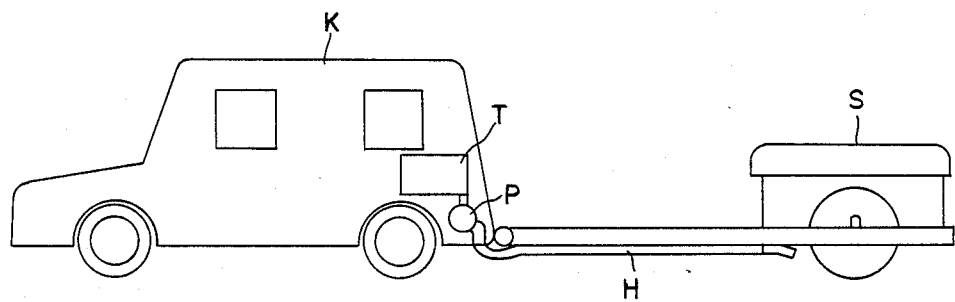
FIG. 5 is a schematic side elevational view illustrating an apparatus for measuring a resistance against slippage on the road surface in accordance with a third embodiment of the present invention.

In addition, as a third embodiment of the present invention, an apparatus as shown in FIG. 5 may be employed which includes a water tank T and a pump P in the tractive vehicle section K so as to allow a predetermined amount of water delivered from the tank T by the pump P to be sprayed ahead of the first and second measuring wheels 2a and 2b via a hose H.

In this embodiment, the apparatus is so constructed that water is sprayed ahead of two measuring wheels as viewed in the direction of movement of the tractive vehicle section. Thus, a thickness of the water film produced by water spraying can be easily controlled by properly controlling an amount of water to be sprayed.

As described hereinabove, since the apparatus of the present invention is so constructed that two measuring wheels rotated by imparting a tractive force thereto are connected to one another via a torsion bar, a difference in number of rotations therebetween is forcibly developed by changing a speed of either of the measuring wheels and a slippage resistance on the road surface is measured by detecting a torque generated on the torsion bar in the presence of a slippage resistance on the road surface, wearing of the measuring wheels can be substantially reduced and the apparatus can enjoy an elongated period of running life. Additionally, the apparatus is simple in structure and measured values having a high reliability are obtainable.

By the way, the fact that measuring is effected only on one line on the road leads to a problem from the viewpoint of maintenance of the road surface. Accordingly, it is preferable that measuring is achieved twice on both the left and right sides of the road to measure a slippage resistance on both the left-hand and right-hand wheel tracks on the road.

However, in a case where a slippage resistance on both the left-hand and right-hand wheel tracks is measured using the above-described apparatus, it is required that the latter runs twice on the same road, causing an operational efficiency to be reduced. Additionally, there arises a problem of hindering a road traffic.

In view of the foregoing problem, description will be made below as to an apparatus for simultaneously measuring a slippage resistance on both the left-hand and right-hand wheel tracks on a road in accordance with a fourth embodiment of the present invention.

Figure 7:
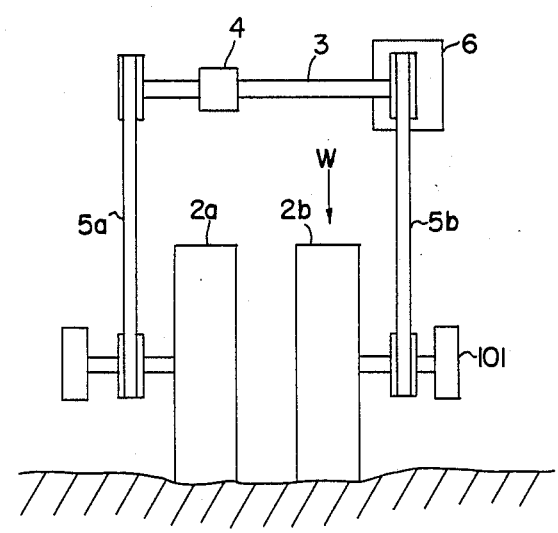
FIG. 7 is a schematic front view illustrating one of units for measuring a slippage resistance on the road surface in the apparatus shown in FIG. 6.
Figure 6:
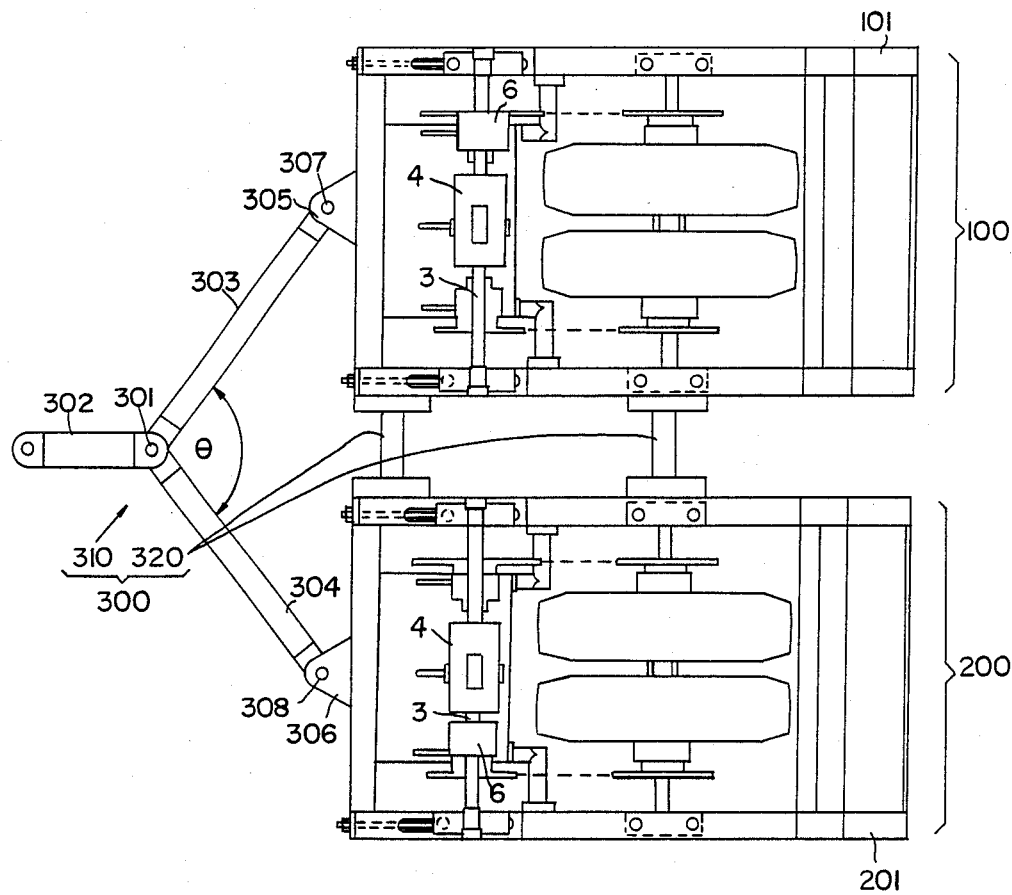
FIG. 6 is a schematic top plan view illustrating an apparatus for measuring a resistance against slippage on the road surface in accordance with a fourth embodiment of the present invention.
Figure 8:
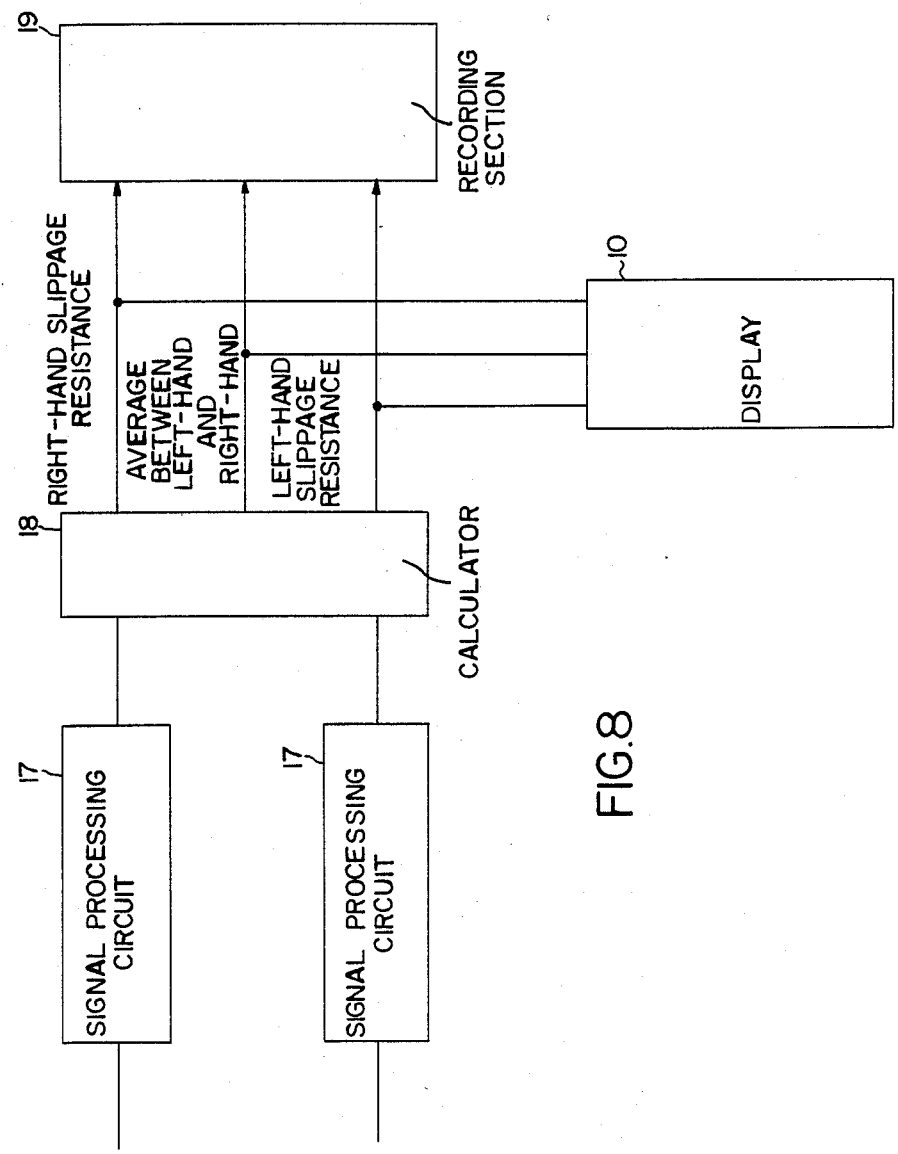
FIG. 8 is a block diagram illustrating a data processing circuit usable for the apparatus shown in FIG. 6.

FIG. 6 is a schematic top plan view of the apparatus, FIG. 7 is a schematic front view of one measuring unit of the apparatus and FIG. 8 is a block diagram illustrating a data processing circuit for the apparatus.

This apparatus includes a first measuring unit 100 and a second measuring unit 200, both units 100 and 200 being supported on first and second unit frames 101 and 201, and it further includes a joint unit 300 for operatively jointing both the units 100 and 200 to one another while adjusting a distance therebetween so that slippage resistances on both the left-hand and right-hand wheel tracks are simultaneously measured while the apparatus is tracted by tracting means (not shown).

The joint unit 300 comprises a joint portion 310 and a mechanism 320 for adjusting measuring positions.

The joint portion 310 comprises a first joint rod 302, a second joint rod 303 and a third joint rod 304 of which one ends are jointed together by a first joint pin 301 so as to permit an angle between the adjacent joint rods to be adjusted as required. The other end of the first joint rod 302 is operatively connected to the tracting means and the other ends of the second and third joint rods 303 and 304 are operatively connected to first and second joint brackets 305 and 306 on the front faces of the first and second unit frames 101 and 201 via first and second joint pins 307 and 308. The apparatus is operatively connected to the tracting means while the first and second unit frames are jointed together.

The mechanism 320 comprises a hydraulic type stroke adjusting mechanism connected to the side faces of the first and second unit frames 101 and 201 so that a distance between the first and second unit frames 101 ans 201 is adjusted so as to allow an angle $\theta$ between the second and third joint rods 303 and 304 to be determined corresponding to the distance therebetween.

Since the first and second units 100 and 200 are same in strucure, it will suffice that description will be made only as to the first unit 100 with reference to FIG. 7. As is apparent from the drawing, the unit 100 comprises a frame 101, first and second measuring wheels 2a and 2b of which shafts are separately supported on the frame 101, a torsion bar 3 and a torque detector 4 for detecting a torque generated on the torsion bar 3. The first measuring wheel 2a is operatively connected to one end of the torsion bar 3 via a first chain transmission mechanism 5a, while the second measuring wheel 2b is operatively connected to the other end of the torsion bar 3 via a second chain transmission mechanism 5b and a speed change gear 6. By reducing the number of rotations of the second measuring wheel 2b, for instance, by 0.8 time via the speed change gear 6, a difference in number of rotations is developed between both the measuring wheels 2a and 2b so that a slippage resistance appearing on the second measuring wheel 2b is detected as a torque generated on the torsion bar 3 using the torque detector 4.

As shown in FIG. 8, outputs from the torque detectors 4 in the first and second slippage resistance measuring units 100 and 200 are transmitted via signal processing circuits 17 to a calculator 18 for calculating a slippage resistance coefficient using a wheel load and a speed reduction ratio as parameters and they are then outputted to a recording section 19 and a displaying section 10 as a right-hand slippage resistance value, a left-hand slippage resistance value and an average value therebetween.

Here, reference character W designates a wheel load. The foremost end of the joint portion is tracted by a tractive force F of the tracting means. A radius R of one of two measuring wheels in each of the units is same to that of the other one. In addition, it is assumed that the speed change gear has a gear ratio of 1:0.8.

Next, operation of the apparatus will be described below.

First, a distance between the first and second slippage resistance measuring units is adjusted as required by the measuring position adjusting mechanism and thereafter the tracting means is activated.

When the tractive force F of the tracting means is transmitted to the first and second unit frames 101 and 201 via the joint portion, the following operation is performed in the respective units.

First, the first measuring wheel 2a is rotated by the tractive force, its rotational force is transmitted to the first chain mechanism 5a and it is transmitted further to the second chain mechanism 5b via the torsion bar 3 and the speed change gear 6 in which speed reduction is achieved whereby it is imparted to the second measuring wheel 2b.

And, this rotational force is transmitted to the road surface.

Due to the fact that a difference in rotation is caused between the first and second measuring wheels, a torque corresponding to a magnitude of friction coefficient on the road surface is generated on the torsion bar.

This torque T is measured by the torque detector and a frictional coefficient μ, that is, a slippage resistance coefficient is calculated in the calculator 18 in accordance with the above-noted formula, and it is displayed in the displaying section while it is recorded in the recording section.

In this manner, a slippage resistance coefficient is simultaneously measured on left-hand and right-hand wheel tracks having a required distance therebetween without substantial hindrance given to a road traffic while both the measuring units run thereon.

Namely, since a distance between the first and second slippage resistance units can be adjusted by the jointing means corresponding to a distance between the left-hand and right-hand wheel tracks to be measured, the respective measuring wheels can be positioned on the left-hand and right-hand wheel tracks in dependence on the current state of the road surface to be measured and moreover a slippage resistance on the left-hand and right-hand wheel tracks can be measured simultaneously.

Additionally, the respective measuring units are such that a slippage resistance is measured separately for them and measurement is made on the basis of the same measuring principle as that shown in the first embodiment.

It should of course be noted that the same advantageous effects as those in the first embodiment are obtainable.

Incidentally, it is preferable that a distance between both the measuring wheels in the respective units is narrow due to the fact that a slippage resistance is measured at a position spaced by about one meter outwardly of the lane mark or the center line on the road and a friction coefficient of the road surface with which one of the measuring wheels come in contact should be same to that of the other one.

In the above-described embodiment, the hydraulic type stroke adjusting mechanism is used as a mechanism for adjusting a measuring position. However, the present invention should not be limited only to this. Of course, other type of adjusting mechanism such as a mechanical type, a pneumatic type or the like may be employed.

In addition, also in the case of the fourth embodiment like in the third embodiment, the tracting means such as a tractive vehicle or the like may be equipped with a water tank and a pump for the purpose of spraying water so as to allow water to be sprayed ahead of the left and right measuring wheels.

As described above, the apparatus of the present invention is so constructed that two measuring wheels adapted to be rotated by imparting a tractive force thereto are connected to one another via a torsion bar, a difference in rotation is forcibly developed between the measuring wheels by changing a rotational speed of one of the measuring wheels, two measuring units are provided to measure a slippage resistance on the road surface by detecting a torque generated on a torsion bar due to the slippage resistance on the road surface and moreover they are connected to one another via a joint unit for allowing them to be adjustably jointed together with a predetermined distance kept therebetween whereby they are tracted via the joint unit. With this construction, a slippage resistance on left-hand and right-hand wheel tracks can be simultaneously measured. Moreover, wearing of both the measuring wheels can be substantially reduced. Another advantageous features are that an elongated period of runnig life is assured, the apparatus is simple in structure and a measured value having a high reliability can be obtained.

What is claimed is:

1. An apparatus for measuring a resistance against slippage on the road surface, characterized in that said apparatus comprises:
   two measuring wheels adapted to be rotated in the same direction on the road surface to be measured, said measuring wheels being tracted by a tractive force,
   a torsion bar attached to said measuring wheels via transmission means for transmitting rotation of said measuring wheels,
   speed changing means attached to at least one of the measuring wheels via said transmission means so as to allow a difference in rotation to be forcibly developed therebetween,
   torque detecting means for detecting a torque generated on said torsion bar due to a slippage resistance attributable to said difference in rotation between said two measuring wheels, and
   calculating means for calculating a slippage resistance coefficient from the detected torque.

2. An apparatus for measuring a resistance against slippage on the road surface claimed in claim 1, characterized in that said two measuring wheels are equipped with water spraying means respectively so as to allow a predetermined amount of water to be sprayed ahead of them as viewed in the direction of movement of the apparatus.

3. An apparatus for measuring a resistance against slippage on the road surface, characterized in that said apparatus comprises;
   a first slippage resistance measuring unit,
   a second slippage resistance measuring unit,
   jointing means for adjustably jointing said first and second slippage resistance measuring units to one another so as to allow them to be tracted with a required distance kept therebetween, and
   tracting means for simultaneously tracting said first and second slippage resistance measuring units via said jointing means,
   wherein each of said slippage resistance measuring units comprises;
   two measuring wheels adapted to be rotated in the same direction on the road surface to be measured, said measuring wheels being tracted by a tractive force,
   a torsion bar for jointing said measuring wheels to one another,
   speed changing means attached to at least one of said measuring wheels so as to allow a difference in rotation to be forcibly developed therebetween, and
   torque detecting means for detecting a torque generated on said torsion bar due to a slippage resistance attributable to said difference in rotation between said two measuring wheels whereby a slippage resistance coefficient is calculated on the basis of the detected torque.

* * * * *